(12) United States Patent
Wang

(10) Patent No.: US 6,268,914 B1
(45) Date of Patent: Jul. 31, 2001

(54) CALIBRATION PROCESS FOR BIREFRINGENCE MEASUREMENT SYSTEM

(75) Inventor: Baoliang Wang, Beaverton, OR (US)

(73) Assignee: Hinds Instruments, Inc., Hillsboro, OR (US)

( * ) Notice: Subject to any disclaimer, the term of this patent is extended or adjusted under 35 U.S.C. 154(b) by 0 days.

(21) Appl. No.: 09/483,708

(22) Filed: Jan. 14, 2000

(51) Int. Cl.$^7$ .................................................. G01J 4/04
(52) U.S. Cl. .............................. 356/365; 356/243.1
(58) Field of Search ................... 356/364–369, 356/33, 32, 243.1, 34, 35, 349, 351, 345; 250/252.1, 225; 73/800; 324/96, 244.1

(56) References Cited

U.S. PATENT DOCUMENTS

| | | |
|---|---|---|
| 3,902,805 | 9/1975 | Redner . |
| 4,362,387 | 12/1982 | Clark . |
| 4,400,062 | 8/1983 | Mori . |
| 4,480,916 | 11/1984 | Bareket . |
| 4,725,145 | 2/1988 | Azzam . |
| 4,801,798 | 1/1989 | Lange . |
| 4,904,931 | 2/1990 | Miller . |
| 4,973,163 | 11/1990 | Sakai . |
| 5,072,111 | 12/1991 | Gilino . |
| 5,268,741 | 12/1993 | Chou . |
| 5,311,284 | 5/1994 | Nishino . |
| 5,457,536 | 10/1995 | Kornfiled . |
| 5,532,823 | 7/1996 | Fukui . |
| 5,536,936 | 7/1996 | Devillon . |
| 5,652,673 | 7/1997 | Oakberg . |
| 5,792,049 * | 8/1998 | Eppstein et al. ................. 600/306 |
| 5,825,492 | 10/1998 | Mason . |
| 5,864,403 | 1/1999 | Ajji . |
| 5,900,939 * | 5/1999 | Aspnes et al. .................. 356/369 |
| 5,956,147 | 9/1999 | Jellison, Jr. . |
| 6,023,332 * | 2/2000 | Bergstrom et al. .............. 356/365 |
| 6,055,053 * | 4/2000 | Lesniak .......................... 356/365 |
| 6,078,042 * | 6/2000 | Fellows .......................... 250/252.1 |

OTHER PUBLICATIONS

Kemp, J.; Piezo–Optical Birefringence Modulators: New Use for a Long–Known Effect; Journal of the Optical Society; vol. 59, No. 8, pp 950–954 (8/1969).

Hinds Instruments; PEM–90 Photoelastic Modulators; Brochure; 10 pages; 1991.

Oakbert, T.; Linear Birefringence and Optical Rotation; Application Note; 5 pages; 1993.

Wang, B. An Improved Method for Measuring Low–Level Linear Birefringence in Optical Materials;SPIE Inorganic Optical Materials Proceedings; vol. 3424; 1998.

Schellman J. et al; Optical Spectroscopy of Oriented Molecules; Chem. Rev. vol. 87, pp1359–1399; May , 1987.

Frattini & Fuller; Phase–Modulated Flow Birefringence; Journal of Rheology; vol. 28; Feb. 1984.

Ohmi et al; High Sensitivity Two–Dimensional Thermal–and Mechanical–stress–Induced Birefringence Measurements in a Nd:Yag Rod.

* cited by examiner

Primary Examiner—Hoa Q. Pham
(74) Attorney, Agent, or Firm—Ipsolon LLP (57) ABSTRACT

A dynamic self calibration process periodically calibrates a system for precisely measuring low-level birefringence properties (retardance and fast axis orientation) of optical materials. Variations in birefringence measurements can be caused by, for example, changes in the environmental conditions ( e.g., ambient pressure or temperature) under which birefringence properties of a sample are measured. In one implementation, the dynamic self calibration process repeatedly calibrates the system at different selected frequencies to compensate for different selected baseline variations.

15 Claims, 9 Drawing Sheets

CALIBRATION PROCESS FOR BIREFRINGENCE MEASUREMENT SYSTEM

TECHNICAL FIELD

This application relates to a system and method for precise measurement of linear birefringence properties of a transparent sample.

BACKGROUND

Many important optical materials exhibit birefringence. Birefringence means that different linear polarizations of light travel at different speeds through the material. These different polarizations are most often considered as two components of the polarized light, one being orthogonal to the other.

Birefringence is an intrinsic property of many optical materials, and may also be induced by external forces. Retardation or retardance represents the integrated effect of birefringence acting along the path of a light beam traversing the sample. If the incident light beam is linearly polarized, two orthogonal components of the polarized light will exit the sample with a phase difference, called the retardance. The fundamental unit of retardance is length, such as nanometers (nm). It is frequently convenient to express retardance in units of phase angle (waves, radians, or degrees) which is proportional to the retardance (nm) divided by the wavelength of the light (nm). An "average" birefringence for a sample is sometimes computed by dividing the measured retardation magnitude by the thickness of the sample.

The two orthogonal polarization components described above are parallel to two orthogonal axes, which are determined by the sample and are called the "fast axis" and the "slow axis." The fast axis is the axis of the material that aligns with the faster moving component of the polarized light through the sample. Therefore, a complete description of the retardance of a sample along a given optical path requires specifying both the magnitude of the retardance and the relative angular orientation of the fast (or slow) axis.

The need for precise measurement of birefringence properties has become increasingly important in a number of technical applications. For instance, it is important to specify and control the residual linear birefringence (hence, the attendant induced retardance) in optical elements used in high precision instruments employed in semiconductor and other industries. The optics industry thus has a need for a highly sensitive instrument for measuring linear birefringence in optical components. This need has been largely unmet, especially with respect to measurements of low levels of retardance.

SUMMARY OF THE INVENTION

The present invention is directed to a practical system and method for precisely measuring low-level birefringence properties of optical materials. The retardance magnitude and orientation of the fast axis are precisely calculated. The system permits multiple measurements to be taken across the area of a sample to detect and graphically display variations in the retardance across the sample area.

In a preferred embodiment, the system incorporates a photoelastic modulator for modulating polarized light that is then directed through a sample. The beam propagating from the sample is separated into two parts. These separate beam parts are then analyzed at different polarization directions, detected, and processed as distinct channels. The detection mechanisms associated with each channel detect the light intensity corresponding to each of the two parts of the beam. This information is employed in an algorithm for calculating a precise, unambiguous measure of the retardance induced by the sample and the orientation of the fast axis.

As one aspect of this invention, the system includes a beam-splitting member and detector arrangement that permits splitting the beam into two parts with minimal contribution to the retardance induced in the beam. Moreover, the presence of any residual birefringence in the optical system (such as may reside as static birefringence in the photoelastic modulator or in any of the optical components of the system) is accounted for in a number of ways. For example, certain of the system components are arranged or mounted to minimize the chance that strain-induced birefringence may be imparted into the element. A reliable calibration technique is also provided.

As another aspect of this invention, the calibration technique includes a dynamic self calibration process by which the system is periodically calibrated to provide an accurate baseline for measuring low-level birefringence properties of optical materials. Variations in the baseline can be caused by, for example, changes in the environmental conditions (e.g., temperature) under which birefringence properties of a sample are measured. In one implementation, the dynamic self calibration process repeatedly calibrates the system at different selected frequencies to compensate for different selected baseline variations.

The system permits the low-level birefringence measurements to be taken at any of a plurality of locations across the area of the sample. The measurements are compiled in a data file and graphically displayed for quick analysis.

In one embodiment of the invention, the optical components of the system are arranged to measure the birefringence properties of a sample that is reflectively coated on one side, thereby permitting measurement of birefringence properties even though the sample is not completely light transmissive.

Other advantages and features of the present invention will become clear upon study of the following portion of this specification and drawings.

BEST MODES FOR CARRYING OUT THE INVENTION

Figures 1, 7:
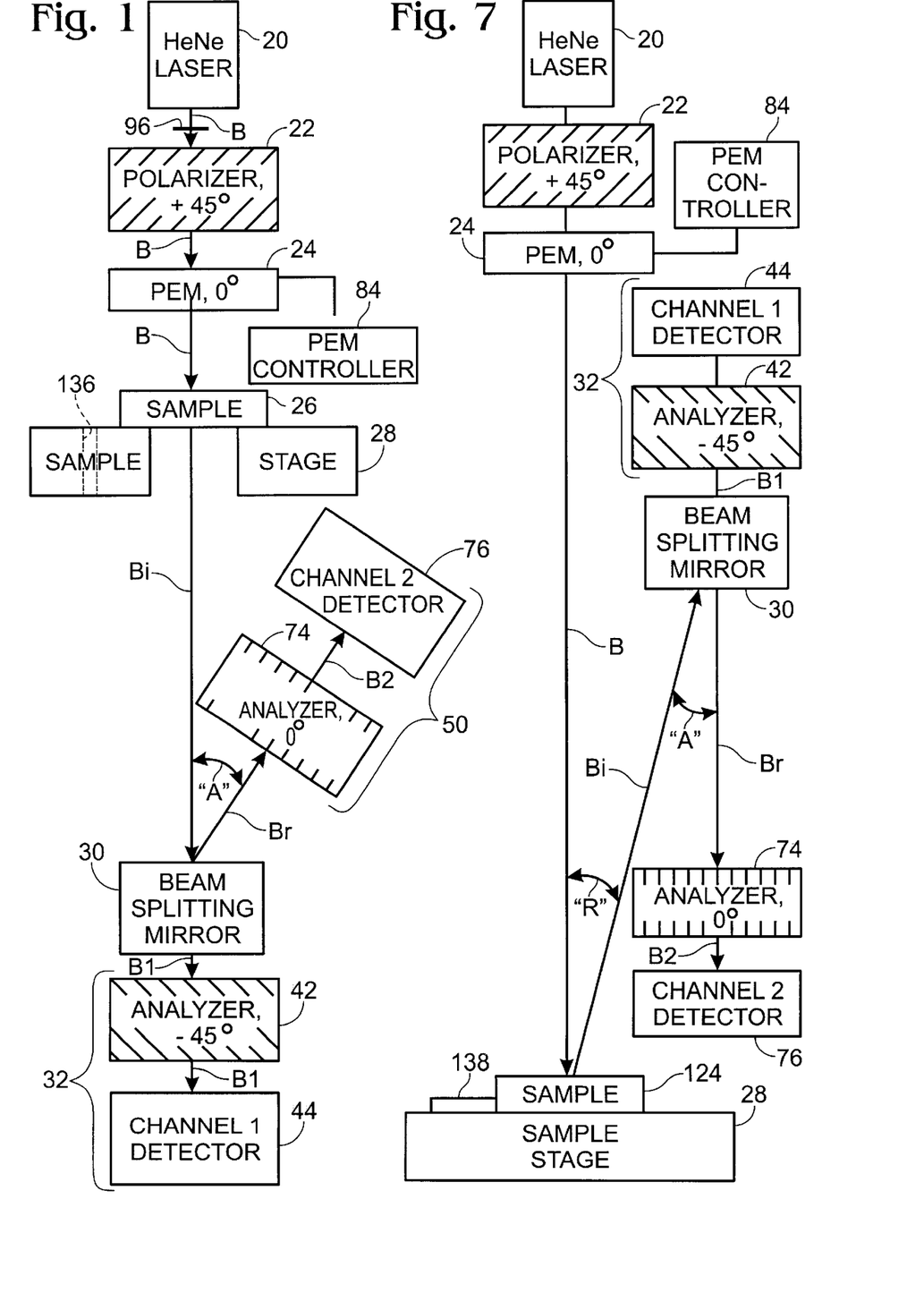
FIG. 1 is a diagram of a preferred embodiment of the present system showing the preferred arrangement of the optical components.
FIG. 7 is a diagram of an alternative embodiment of the present invention.

The diagram of FIG. 1 depicts the primary optical components of a system made in accordance with the present invention. The components include a HeNe laser as a light source 20 that has a wavelength of 632.8 nanometers (nm). The beam "B" emanating from the source has a cross sectional area or "spot size" of approximately 1 millimeter (mm).

The source light beam "B" is directed to be incident on a polarizer 22 that is oriented with its polarization direction at +45° relative to a baseline axis. A high-extinction polarizer, such as a Glan-Thompson calcite polarizer, is preferred. It is also preferred that the polarizer 22 be secured in a precision, graduated rotator.

Figure 5:
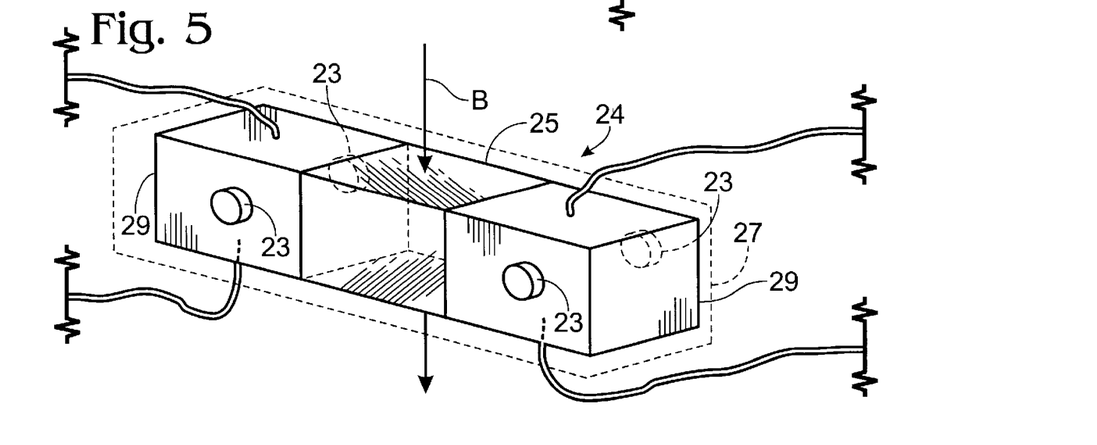
FIG. 5 is a perspective view of the primary components of a photoelastic modulator that is incorporated in the present system.

The polarized light from the polarizer 22 is incident on the optical element 25 of a photoelastic modulator 24 (FIGS. 1 and 5). In a preferred embodiment, the photoelastic modulator (hereafter referred to as a "PEM") is one manufactured by Hinds Instruments, Inc., of Hillsboro, Oreg., as a low birefringence version of Model PEM-90 I/FS50. It is noteworthy here that although a PEM is preferred, one could substitute other mechanisms for modulating the polarization of the source light.

The PEM has its birefringent axis oriented at 0° and is controlled by a controller 84 that imparts an oscillating birefringence to the optical element 25, preferably at a nominal frequency of 50 kHz. In this regard, the controller 84 drives two quartz transducers 29 between which the optical element 25 is bonded with an adhesive.

The oscillating birefringence of the PEM introduces a time-varying phase difference between the orthogonal components of the polarized light that propagates through the PEM. At any instant in time, the phase difference is the retardation introduced by the PEM. The retardation is measurable in units of length, such as nanometers. The PEM is adjustable to allow one to vary the amplitude of the retardation introduced by the PEM. In the case at hand, the retardation amplitude is selected to be 0.383 waves (242.4 nm).

The beam of light propagating from the PEM is directed through the transparent sample 26. The sample is supported in the path of the beam by a sample stage 28 that is controllable for moving the sample in a translational sense along orthogonal (X and Y) axes. The stage may be any one of a number of conventional designs such as manufactured by THK Co. Ltd., of Tokyo, Japan as model KR2602 A-250. As will become clear, the motion controllers of the sample stage 28 are driven to enable scanning the sample 26 with the beam to arrive at a plurality of retardance and orientation measurements across the area of the sample.

The sample 26 will induce retardance into the beam that passes through it. It is this retardance value that is determined in accordance with the processing provided by the present invention, as explained more below. The present system is especially adapted to determine low levels of retardance. Low retardance levels are determined with a sensitivity of less than ±0.01 nm.

In order to obtain an unambiguous measure of the sample-induced retardance, the beam "Bi" that passes out of the sample is separated into two parts having different polarization directions and thereby defining two channels of information for subsequent processing.

Turning first to the preferred mechanism for separating the beam "Bi," there is located in the path of that beam (hereafter referred to as the incidence path) a beam-splitting mirror 30. Part "B1" of the beam "Bi" passes completely through the beam-splitting mirror 30 and enters a detector assembly 32 for detection.

Figure 3:
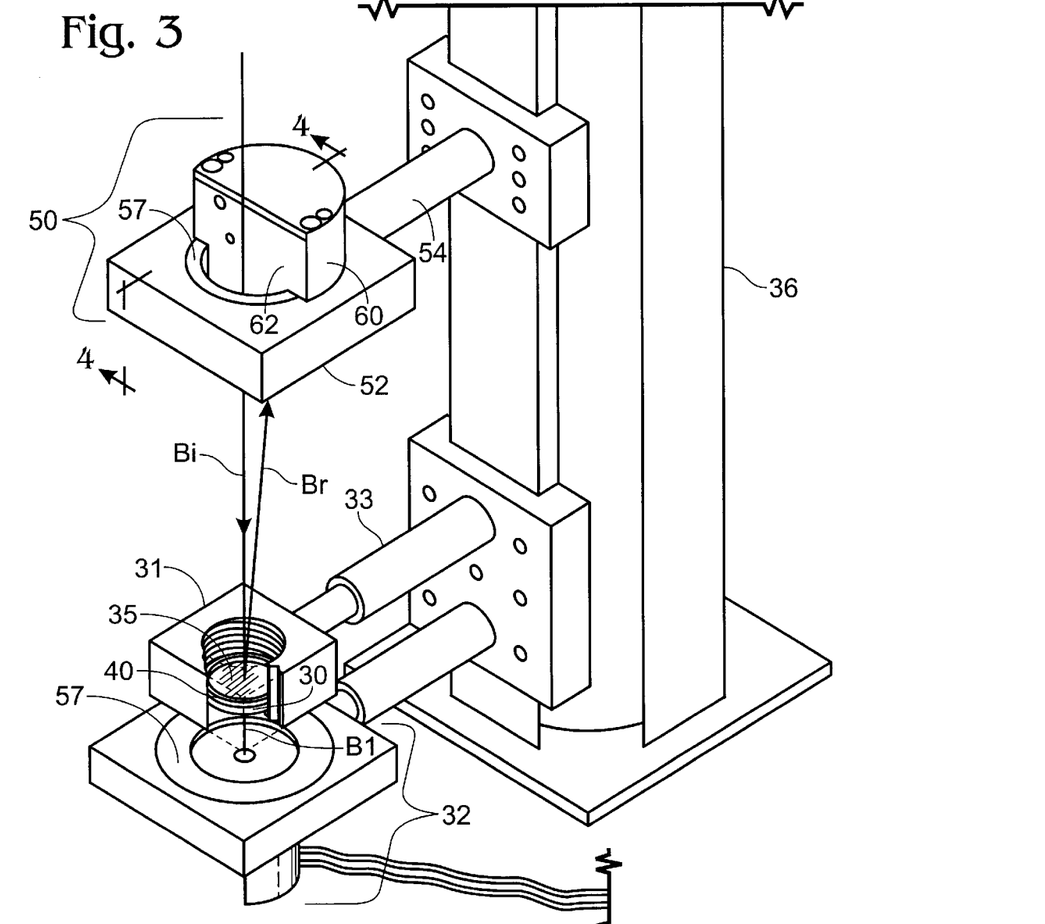
FIG. 3 is a perspective view of detection and beam-splitting components of the system.

FIG. 3 depicts a preferred mechanism for supporting the beam-splitting mirror 30. In particular, the mirror 30 is seated in the central aperture of a housing 31 that is rigidly supported by an arm 33 to a stationary vertical post 36. The post 36 is employed for supporting all of the optical components of the system so that the paths of the light are generally vertical.

The diameter of the mirror 30 is slightly less than the diameter of the housing aperture. The aperture is threaded except for an annular shoulder that projects into the lowermost end of the aperture to support the periphery of the flat, round mirror 30. A retainer ring 40 is threaded into the aperture to keep the mirror in place in the housing 31 against the shoulder.

In a preferred embodiment, care is taken to select and mount the mirror 30 so that substantially no stress-induced birefringence is introduced into the mirror. In this regard, the mirror is preferably made of Schott Glass type SF-57 glass. This glass has an extremely low (near zero) stress-optic coefficient. The retainer ring 40 is carefully placed to secure the mirror without stressing the glass. Alternatively, flexible adhesive may be employed to fasten the mirror. No set-screws or other stress-inducing mechanisms are employed in mounting the mirror.

It is noteworthy here that, although a beam-splitting mirror is preferred, one can substitute other mechanisms (such as a flipper mirror arrangement) for separating the beam "Bi" into two parts.

The part of the beam "B1" that passes through the mirror 30 enters the detector assembly 32 (FIG. 1), which includes a compact, Glan-Taylor type analyzer 42 that is arranged such that its polarization direction is at −45° from the baseline axis. From the analyzer 42, the beam "B1" enters a detector 44, the particulars of which are described more below.

The reflective surface 35 of the beam-splitting mirror 30 (FIG. 3) faces upwardly, toward the sample 26. The mirror is mounted so that the incidence path (that is, the optical path of the beam "Bi" propagating from the sample 26) is nearly normal to the reflective surface 35. This orientation is preferred for substantially eliminating retardance that would otherwise be introduced by an optical component that is called on to redirect the path of the beam by more than a few degrees.

FIG. 1 shows as "A" the angle made between the beam "Bi" travelling along the incidence path and the beam part "Br" that is reflected from the mirror 30. Angle "A" is shown greatly enlarged for illustrative purposes. In a preferred embodiment, this angle is greater than 0° but less than 10°. Most preferred is an angle "A" of under 5°.

The reflected part of the Beam "Br" is incident upon another detector assembly 50. That assembly 50 is mounted to the post 36 (FIG. 3) and configured in a way that permits the assembly to be adjacent to the incident beam "Bi" and located to receive the reflected beam "Br." More particularly, the assembly 50 includes a base plate 52 that is held to the post 36 by an arm 54. As seen best in FIG. 4, the base plate includes an inner ring 57 that is rotatably mounted to the base plate and has a large central aperture 56 that is countersunk to define in the bottom of the plate 52 an annular shoulder 58.

Figure 4:
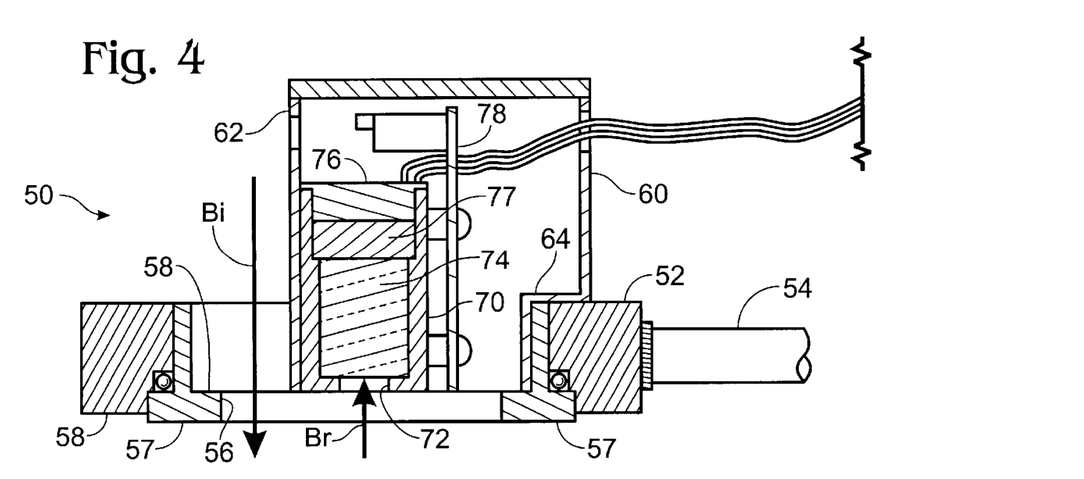
FIG. 4 is a cross-sectional view of one of the detector assemblies of the system.

The detector components are compactly integrated and contained in a housing 60 that has a flat front side 62. The remainder of the side of the housing is curved to conform to the curvature of the central aperture 56 of the base plate 52. Moreover, this portion of the housing 60 includes a stepped part 64 that permits the curved side of the housing to fit against the base plate 52 and be immovably fastened thereto.

A sub-housing 70 is fastened inside of the detector components housing 60 against the flat side 62. The sub-housing 70 is a generally cylindrical member having an aperture 72 formed in the bottom. Just above the aperture 72 resides a compact, Glan-Taylor type analyzer 74 that is arranged so that its polarization direction is 0°, parallel with that of the PEM 24.

Stacked above the analyzer 74 is a narrow-band interference filter 77 that permits passage of the polarized laser light but blocks unwanted room light from reaching a detector 76. The detector is preferably a photodiode that is stacked above the filter. The photodiode detector 76 is the preferred detection mechanism and produces as output a current signal representative of the time varying intensity of the received laser light. With respect to this assembly 50, the laser light is that of the beam "B2," which is the reflected part "Br" of the beam that propagated through the sample 26.

The photodiode output is delivered to a preamplifier carried on an associated printed circuit board 78 that is mounted in the housing 60. The preamplifier 75 (FIG. 2) provides output to a phase sensitive device (preferably a lock-in amplifier 80) in the form of a low-impedance intensity signal $V_{AC}$, and a DC intensity signal $V_{DC}$, which represents the time average of the detector signal.

It is noteworthy here that the other detector assembly 32 (FIG. 3) to which is directed the non-reflected part "B1" of the beam "Bi" is, except in two respects, the same construction as the just described assembly 50. As shown in FIG. 3, the detector assembly 32 is mounted to the post 36 in an orientation that is generally inverted relative to that of the other detector assembly 50. Moreover, the analyzer 42 of that assembly 32 is arranged so that its polarization direction is oblique to the polarization direction of the analyzer 74 in the other detector assembly 50. Specifically, the analyzer 42 is positioned with its polarization direction at −45°. The preferred analyzer position is established by rotating the detector assembly via the inner ring 57 discussed above.

The photodiode of detector assembly 32 produces as output a current signal representative of the time varying intensity of the received laser light. With respect to this assembly 32, the laser light is that of the beam "B1," which is the non-reflected part of the beam "Bi" that propagated through the sample 26.

The photodiode output of the detector assembly 32 is delivered to a preamplifier 79, which provides its output to the lock-in amplifier 80 (FIG. 2) in the form of a low-impedance intensity signal $V_{AC}$, and a DC intensity signal $V_{DC}$, which represents the time average of the detector signal.

In summary, the lock-in amplifier 80 is provided with two channels of input: channel 1 corresponding to the output of detector assembly 32, and channel 2 corresponding to the output of detector assembly 50. The intensity information received by the lock-in amplifier on channel 1—because of the arrangement of the −45° analyzer 42—relates to the 0° or 90° component of the retardance induced by the sample 26. The intensity information received on channel 2 of the lock-in amplifier 80—as a result of the arrangement of the 0° analyzer 74—relates to the 45° or−45° component of the retardance induced by the sample. As explained below, this information is combined in an algorithm that yields an unambiguous determination of the magnitude of the overall retardance induced in the sample (or a location on the sample) as well as the orientation of the fast axis of the sample (or a location on the sample).

Figure 2:
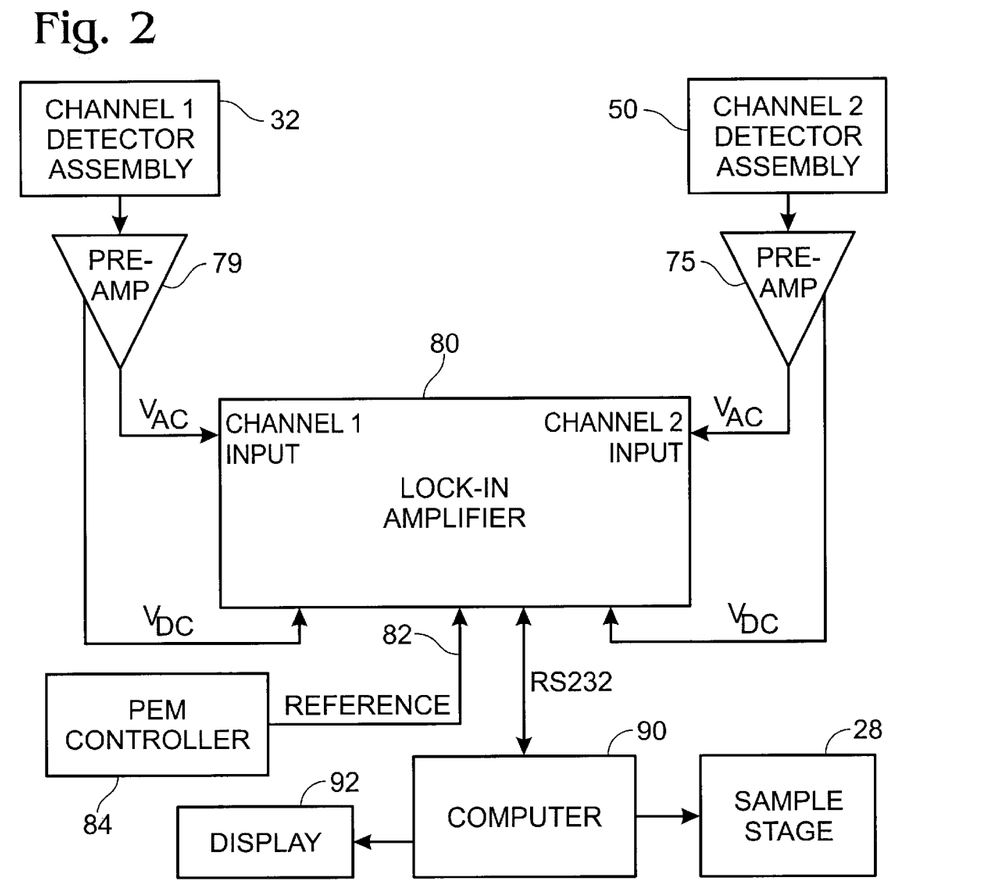
FIG. 2 is a block diagram of the processing components of the present system.

The lock-in amplifier 80 may be one such as manufactured by EG&G Inc., of Wellesley, Mass., as model number 7265. The lock-in amplifier takes as its reference signal 82 the oscillation frequency applied by the PEM controller 84 to the transducers 29 that drive the optical element 25 of the PEM 24. The lock-in amplifier 80 communicates with a digital computer 90 via an RS232 serial interface.

For a particular retardance measurement, such as one taken during the scanning of several locations on a sample, the computer 90 obtains the values of channel 1. The computer next obtains the values of channel 2. The intensity signals on the detectors in channels 1 and 2 are derived as follows:

$$I_{ch1}=[1+\cos(4\rho)\sin^2[\delta/2]\cos \Delta-\cos^2[\delta/2]\cos \Delta+\cos(2\rho)\sin \delta \sin \Delta]I_0/2$$
$$I_{ch2}=[1+\sin(4\rho)\sin^2[\delta/2]\cos \Delta+\sin(2\rho)\sin \delta \sin \Delta]I_0/2 \qquad \text{eqn. (1)}$$

where $\Delta$ is the PEM's time varying phase retardation; $\delta$ is the magnitude of the sample's retardance; $\rho$ is the azimuth of the fast axis of the sample's retardance, and $I_0$ is the initial intensity of the light before it reaches the PEM. The Mueller matrix for a linearly birefringent sample ($\delta$, $\rho$) used in the derivation has the following form:

$$\begin{bmatrix} 1 & 0 & 0 & 0 \\ 0 & \cos(4\cdot\rho)\cdot\sin\left(\frac{\delta}{2}\right)^2 + \cos\left(\frac{\delta}{2}\right)^2 & \sin(4\cdot\rho)\cdot\sin\left(\frac{\delta}{2}\right)^2 & -\sin(2\cdot\rho)\cdot\sin(\delta) \\ 0 & \sin(4\cdot\rho)\cdot\sin\left(\frac{\delta}{2}\right)^2 & -\left(\cos(4\cdot\rho)\cdot\sin\left(\frac{\delta}{2}\right)^2\right)+\cos\left(\frac{\delta}{2}\right)^2 & \cos(2\cdot\rho)\cdot\sin(\delta) \\ 0 & \sin(2\cdot\rho)\cdot\sin(\delta) & -(\cos(2\cdot\rho)\cdot\sin(\delta)) & \cos(\delta) \end{bmatrix}$$

In equations (1), $\sin\Delta$ ($\Delta=\Delta_0 \sin\omega t$, where $\omega$ is the PEM's modulating frequency; $\Delta_0$ is the maximum peak retardance of the PEM) can be expanded with the Bessel functions of the first kind:

$$\sin\Delta = \sin(\Delta_0 \sin(\omega t)) = \sum_{2k+1} 2J_{2k+1}(\Delta_0)\sin((2k+1)\omega t) \quad \text{eqn. (2)}$$

where k is either "0" or a positive integer; and $J_{2k+1}$ is the (2k+1)th order of the Bessel function. Similarly, $\cos\Delta$ can be expanded with the even harmonics of the Bessel functions:

$$\cos\Delta = \cos(\Delta_0 \sin(\omega t)) = J_0(\Delta_0) + \sum_{2k} 2J_{2k}(\Delta_0)\cos((2k)\omega t) \quad \text{eqn. (3)}$$

where $J_0$ is the $0^{th}$ order of the Bessel function, and $J_{2k}$ is the (2k)th order of the Bessel function.

As seen from eqns. 1–3, it is preferable to determine the magnitude and angular orientation of retardance using the signal at the PEM's first harmonic. The useful signal for measuring linear birefringence at the PEM's 2nd harmonic is modified by $\sin^2(\delta/2)$, a value that is much smaller than $\sin\delta$. The 1F electronic signal on the detectors can be expressed in equation (4):

$$I_{ch1,1F} = [\sin\delta\cos(2\rho)2J_1(\Delta_0)\sin(\omega t)]\frac{I_0}{2} \quad \text{eqn. (4)}$$

$$I_{ch2,1F} = [\sin\delta\sin(2\rho)2J_1(\Delta_0)\sin(\omega t)]\frac{I_0}{2}$$

As noted, the 1F signal is determined using the lock-in amplifier 80 that is referenced at the PEM's first harmonic. The lock-in amplifier will exclude the contributions from all harmonics other than 1F. The output from the lock-in amplifier 80 for the two channels is:

$$I_{ch1}(1F) = \frac{I_0}{2\sqrt{2}}\delta\cos(2\rho)2J_1(\Delta_0) \quad \text{eqn. (5)}$$

$$I_{ch2}(1F) = \frac{I_0}{2\sqrt{2}}\delta\sin(2\rho)2J_1(\Delta_0)$$

using the approximation of $\sin\delta\approx\delta$ for low-level linear birefringence; and $\sqrt{2}$ results from the fact that the lock-in amplifier measures the r.m.s. of the signal, instead of the amplitude.

All terms appearing at a frequency other than the PEM's first harmonic are neglected in obtaining equations (5). The validity of equations (5) for obtaining the 1F $V_{AC}$ signal is further ensured from the approximation that $\sin^2(\delta/2)\approx 0$ when $\delta$ is small. This applies for low-level retardance of, for example, less than 20 nm.

In order to eliminate the effect for intensity fluctuation of the light source, or variations in transmission due to absorption, reflection losses, or scattering, the ratio of the 1F $V_{AC}$ signal to the $V_{DC}$ signal is used. (Alternatively, similar techniques can be employed, such as dynamically normalizing the DC signal to unity.) Exclusion of the $\cos\Delta$ terms in equation (1) can severely affect the $V_{DC}$ signal in channel 1 even though it has a minimal effect on the determination of the 1F $V_{AC}$ signal using a high quality lock-in amplifier. The term $\cos^2(\delta/2)\cos\Delta$ in equation (1) is approximately equal to $\cos\Delta$ for small $\delta$. As seen from equation (3), $\cos\Delta$ depends on $J_0(\Delta_0)$, which is a "DC" term. Consequently, this DC term should be corrected as in equations (7):

$$\frac{I_{ch1}(1F)}{I_{dc(ch1)}} \cdot \frac{1-J_0(\Delta_0)}{2J_1(\Delta_0)} \cdot \sqrt{2} = R_{ch1} = \delta\cos(2\rho) \quad \text{eqn. (7)}$$

$$\frac{I_{ch2}(1F)}{I_{dc(ch2)}} \cdot \frac{1}{2J_1(\Delta_0)} \cdot \sqrt{2} = R_{ch2} = \delta\sin(2\rho)$$

where $R_{ch1}$ and $R_{ch2}$ are experimentally determined quantities from the two channels.

To correct the "DC" term caused by the $\cos\Delta$ term in channel 1, one properly sets the PEM retardation so that $J_0(\Delta_0)=0$ (when $\Delta_0=2.405$ radians, or 0.383 waves). At this PEM setting, the efficiency of the PEM for generating the 1F signal is about 90% of its maximum.

Finally, the magnitude and angular orientation of the linear birefringence is expressed in equations (8):

$$\rho = \frac{1}{2}\tan^{-1}\left[\frac{R_{ch2}}{R_{ch1}}\right] \text{ or } \rho = \frac{1}{2}ctg^{-1}\left[\frac{R_{ch1}}{R_{ch2}}\right] \quad \text{eqn. (8)}$$

$$\delta = \sqrt{(R_{ch1})^2 + (R_{ch2})^2}$$

These equations (8) are compiled in a program running on the computer 90 and used to determine the magnitude and orientation of the retardance at any selected point on the sample.

Equations (8) are specifically developed for small linear birefringence. The approximation of $\sin\delta\approx\delta$ used in deriving equations (8) has an error of ~1% for $\delta=20$ nm when the light wavelength is at 632.8 nm. For any larger retardation, $\sin\delta$ should be used, instead of $\delta$.

As noted above, best retardance measurement results are achieved when one minimizes the residual birefringence present in the optical components of the system. To this end, the present system employs a PEM 24 (FIG. 5) that is specially configured to eliminate residual birefringence that may be attributable to supporting the optical element 25 of the PEM in the housing 27 (shown in dashed lines of FIG. 5). The bar-shaped optical element is bonded at each end to a transducer 29. Each transducer 29 is mounted to the PEM housing 27, as by supports 23, so that the optical element is essentially suspended, thus free from any residual birefringence that may be attributable to directly mounting the oscillating optical element 25 to the PEM housing 27.

Notwithstanding efforts such as the foregoing to eliminate residual birefringence in the system components, the presence of at least some level of residual birefringence is inevitable. In the present system, highly accurate results are obtained by correcting the results of equations 8 to account for any remaining residual birefringence in the system, which residual may be referred to as the system offset. In practice, residual birefringence in the optical element of the photoelastic modulator and in the beam-splitting mirror substrate can induce errors in the resulting measurements. Any such errors can be measured by first operating the system with no sample in place. A correction for the errors is made by subtracting the error values for each channel.

The system offset is obtained by making a measurement without a sample in place. The results from both channels 1 and 2 are the system offsets at 0° and 45° respectively:

$$R^0_{ch1} = \frac{I^0_{ch1}(1F)\sqrt{2}}{2J_1(\Delta_0)I^0_{dc1}} = \delta^0(\rho = 0)$$

$$R^0_{ch2} = \frac{I^0_{ch2}(1F)\sqrt{2}}{2J_1(\Delta_0)I^0_{dc2}} = \delta^0(\rho = \frac{\pi}{4})$$

eqn. (9)

where the superscript "0" indicates the absence of a sample. The equation bearing the term $\rho=0$ corresponds to channel 1 (the −45° analyzer 42). The equation bearing the term $\rho=\pi/4$ corresponds to channel 2 (the 0° analyzer 74). The system offsets are corrected for both channels when a sample is measured. The system offsets for channels 1 and 2 are constants (within the measurement error) at a fixed instrumental configuration. Barring any changes in the components of the system, or in ambient pressure or temperature, the system should remain calibrated.

In principle, this procedure will provide a method of self calibration of the system. It is, however, prudent to compare the system measurement of a sample with the measurement obtained using other methods.

One such calibration sample may be provided by a compound zero-order waveplate. The compound waveplate comprises two multiple-order waveplates (e.g., quartz) or two zero-order waveplates (e.g., mica) selected to have a very small retardance difference between them (e.g., less than 0.03 wavelengths). They would be combined with their axes at right angles so that the retardance of one is subtracted from the other to produce the sought-after low-level retardance, compound zero-order waveplate(s) for use in calibration. Such a configuration will provide a uniform retardance across the surface with a low temperature coefficient of retardance.

If the components of the present system are correctly set up, the magnitude of the measured, sample-induced retardance will be independent of the sample's angular orientation. This angular independence may be lost if: (1) the polarization directions of the polarizer 22 and analyzers 42, 74 are not precisely established, and (2) the maximum peak retardance of the PEM is not precisely calibrated. What follows is a description of correction techniques for eliminating the just mentioned two sources of possible "angular dependence" errors.

As respects the precise establishment of the polarization directions of the polarizer 22 and analyzers 42, 74, the correction technique applied to the polarizer 22 involves the following steps:

1. With the PEM operating, approximately orient the polarizer 22 and the channel 1 analyzer/detector assembly 32 at 45° and −45°, respectively.
2. Rotate the polarizer 22 in fine increments while monitoring the 2F (100 kHz) lock-in amplifier signal from channel 1. When the 2F signal reaches "0" (practically, the noise level at the highest lock-in amplifier sensitivity possible), read precisely the angle on the polarizer rotator.
3. Rotate the polarizer 22 by precisely 45°, which is the correct position for the polarizer.
4. Once the position of the polarizer 22 is correctly established, turn off the PEM and rotate analyzer/detector assembly 32 while monitoring the lock-in amplifier's $V_{DC}$ signal from channel 1. When the minimum $V_{DC}$ signal is achieved, the position of analyzer/detector assembly 32 is set correctly.
5. Once the position of the polarizer 22 is correctly established, rotate analyzer/detector assembly 50 while monitoring the lock-in amplifier's 2F (100 kHz) signal from channel 2. When this 2F signal reaches "0" (practically, the noise level at the highest lock-in amplifier sensitivity possible), the position of analyzer/detector assembly 50 is set correctly.

As respects the calibration of the PEM, the following technique may be employed:

1. Set the channel 1 analyzer/detector assembly 32 at −45° when the polarizer 22 is at +45°.
2. Record the $V_{DC}$ signals with a precision voltmeter while the PEM retardance is changed in the vicinity of, for example, ±10% of the selected peak retardance of the PEM.
3. Set the channel 1 analyzer/detector assembly 32 at +45°.
4. Record $V_{DC}$ signals with a precision voltmeter while the PEM retardance is changed in the selected vicinity.
5. Plot the two $V_{DC}$ curves against PEM retardance around the selected peak retardance. The intersection of the two curves is the retardance for $J_0=0$.
6. Set the PEM retardance value at the intersection value of step 5.

As mentioned above, the motion controllers of the sample stage 28 are controlled in a conventional manner to incrementally move the sample 26 about orthogonal (X, Y) axes, thereby to facilitate a plurality of measurements across the area of a sample. The spatial resolution of these measurements can be established as desired (e.g., 3.0 mm), provided that the sought-after resolution is not finer than the cross section of the beam that strikes the sample. In this regard, the cross sectional area or "spot size" of the laser beam may be minimized, if necessary, by the precise placement of a convex lens with an appropriate focal length, such as shown as line 96 in FIG. 1, between the light source 20 and the polarizer 22. The lens could be, for example, removably mounted to the top of the polarizer 22. The lens 96 would be in place in instances where a very small spot size of, for example, 0.1 mm (and corresponding spatial resolution) is desired for a particular sample.

In some instances it may be desirable to enlarge the spot size provided by the laser source. To this end a lens or lens system such as provided by a conventional beam expander may be introduced into the system between the laser 20 and the polarizer 22.

Figure 6:
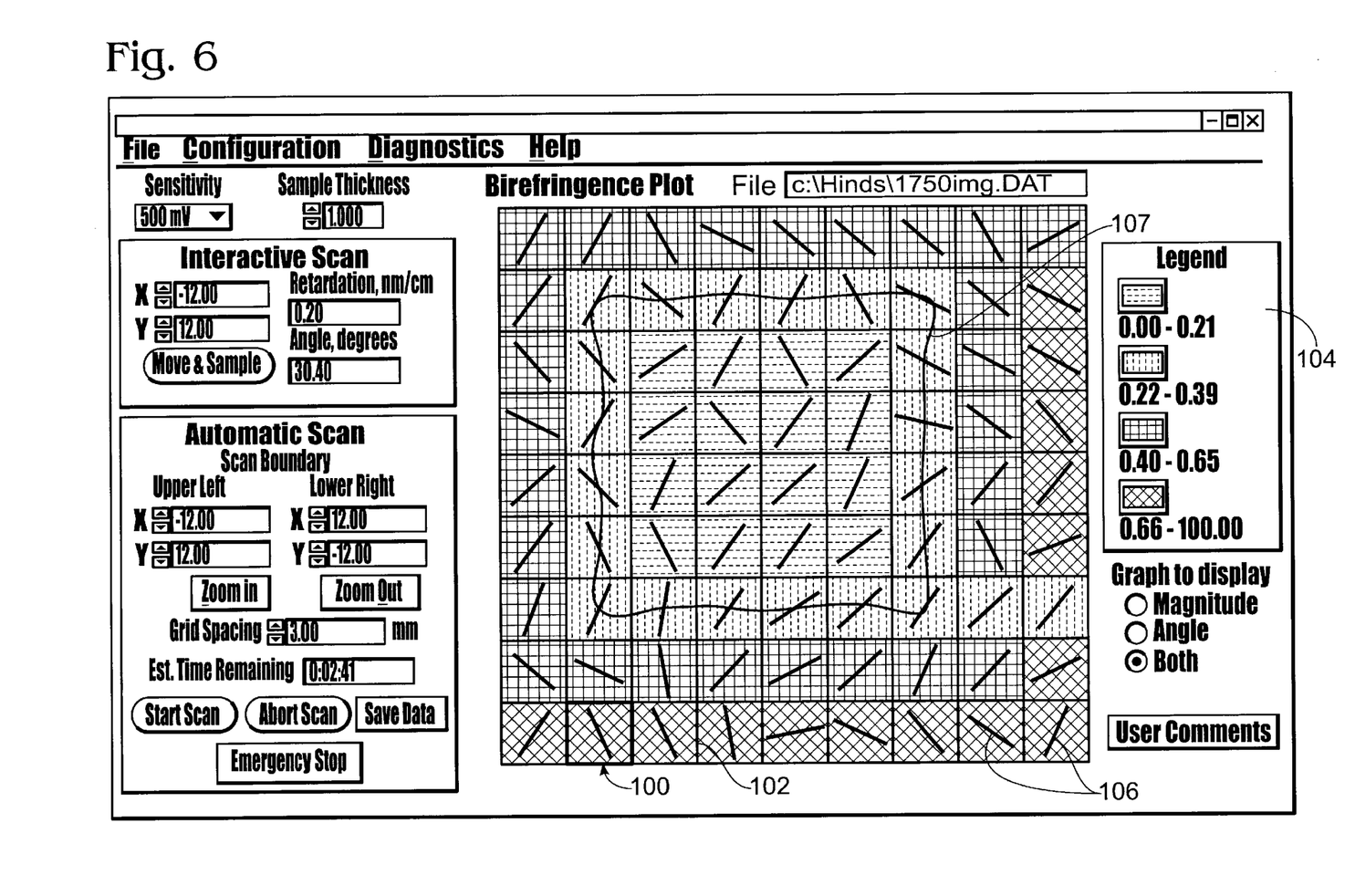
FIG. 6 is a drawing depicting a graphical display provided by the system of the present invention.

The measured retardance values can be handled in a number of ways. In a preferred embodiment the data collected from the multiple scans of a sample are stored in a data file and displayed as a plot on a computer display 92. One such plot 100 is shown in FIG. 6. Each cell 102 in a grid of cells in the plot indicates a discrete location on the sample. The magnitude of the retardance is depicted by color coding. Here different shadings in the cells represent different colors. In FIG. 6, only a few different colors and cells are displayed for clarity. It will be appreciated, however, that a multitude of cells can be displayed. The legend 104 on the display correlates the colors (the color shading is omitted from the legend) to a selectable range of retardance values within which the particular measurement associated with a cell 102 falls. A line 106 located in each cell 102 extends across the center of each cell and presents an unambiguous visual indication of the full physical range (−90° to +90°) of the orientation of the fast axis of the sample at each sampled location. Thus, the orientation of the fast axis and the retardance magnitude measurements are simultaneously, graphically displayed for each location. With such a complete, graphical display, an inexperienced operator user is less likely to make errors in analyzing the data that are presented.

In a preferred embodiment, the just described retardance measurements are displayed for each cell as soon as that cell's information is computed. As a result of this instantaneous display approach, the operator observes the retardance value of each cell, without the need to wait until the retardance values of all of the cells in the sample have been calculated. This is advantageous for maximizing throughput in instances where, for example, an operator is charged with rejecting a sample if the birefringence value of any part of the sample exceeds an established threshold.

Also illustrated in FIG. 6 is a contour line placed there as an example of a contour line that follows a common measured range of retardation magnitude. For simplicity, only a single one of several contour lines is shown for the low-resolution plot of FIG. 6.

It will be appreciated that any of a number of variations for displaying the measured data will suffice. It will also be apparent from FIG. 6 that the means for setting parameters of how the sample is scanned (scan boundaries, grid spacing sample thickness, etc.) and the resulting data are conveniently, interactively displayed.

Another approach to graphically displaying the retardance magnitude and orientation information provided by the present system is to depict the retardance magnitude for a plurality of locations in a sample via corresponding areas on a three-dimensional contour map. The associated orientations are simultaneously shown as lines or colors in corresponding cells in a planar projection of the three dimensional map.

FIG. 7 depicts an arrangement for measuring retardance magnitude and orientation in a sample 124 that is reflectively coated on one side. Apart from the different sample 124 and the relative locations of the optical components, the components of the system of FIG. 7 match those of the embodiment of FIG. 1 and thus carry the same reference numbers, with a few exceptions as noted below.

The sample 124 (FIG. 7) is coated on one side with a reflective surface, such as very thin layer of chromium. The sample is placed on the sample stage with the coated surface on the bottom. The beam "B" is directed to pass through the sample 124. The sample stage is slightly tilted (or, alternatively, the sample is secured in a tilted holder mounted to a flat stage) so that the beam reflects from the coated surface toward the beam-splitting mirror 30 and detector assembly 32, which are, in this embodiment, supported above the sample stage 28 as shown. Preferably, these components are located as near as practical to the beam "B" so that the beam "Bi" reflected from the sample 124 is angled "R" only slightly away (for example 2° to 5°) from the beam "B" propagating from the PEM 24. The beam reflected by the sample (as distinguished from the beam "Br" reflected by the mirror 30) corresponds, from a processing standpoint, to the beam "Bi" impinging on the mirror 30 of the FIG. 1 embodiment. Thus, the processing of the two beam parts "B1" and "B2" are the same for both embodiments. Of course, the measured retardance magnitude of the sample 124 will necessarily comprise two passes of the beam through the sample. Therefore the measured value will be divided by two.

As noted above, it is desirable to locate the beam-splitting mirror 30 as near as practical to the beam "B" so that the beam "Bi" reflected from the sample 124 is angled "R" only slightly away (for example 2° to 5°) from the beam "B" propagating from the PEM 24. To this end, the housing 31 may be modified to support a mirror that is semi-circular in shape such that the flat edge of the mirror is located adjacent to the beam "B." The beam "Bi", therefore, could be reflected to a location on the mirror that is very close to that edge, hence to the beam "B" as desired.

While the present invention has been described in terms of preferred embodiments, it will be appreciated by one of ordinary skill in the art that modifications may be made without departing from the teachings and spirit of the foregoing. For example a second lock-in amplifier may be employed (one for each channel) for increasing the speed with which data is provided to the computer.

Also, one of ordinary skill will appreciate that sequential measurement using a single detector may be employed for measuring the intensity signal in two different polarization directions and thereby defining two channels of information for subsequent processing. For example, a single detector assembly could be employed. This dispenses with the second detector assembly and the beam-splitter mirror. Such a set-up, however, would require either rotating the analyzer or switching between two polarizers of different orientations to ensure unambiguous retardance measurements and to ascertain the orientation of the fast axis. Alternatively, the sample and the analyzer may be rotated by 45°.

The preferred embodiment of the present invention uses a HeNe laser for a stable, pure, monochromatic light source. The HeNe laser produces a beam having a 632.8 nm wavelength. In some instances, retardance magnitude measurements using light sources having other frequencies are desired.

As another aspect of the present invention, one can develop and apply correction factors to convert the retardance magnitude measurement of the sample as measured by the HeNe laser to the retardance value that would occur in the sample at another source-light wavelength. In this regard, FIG. 8 charts experimental results showing the oscillation amplitude required to produce, via the PEM, a selected peak retardation (such as half-wave) plotted against different source wavelengths for a PEM that employs a fused silica type optical element.

Figure 8:
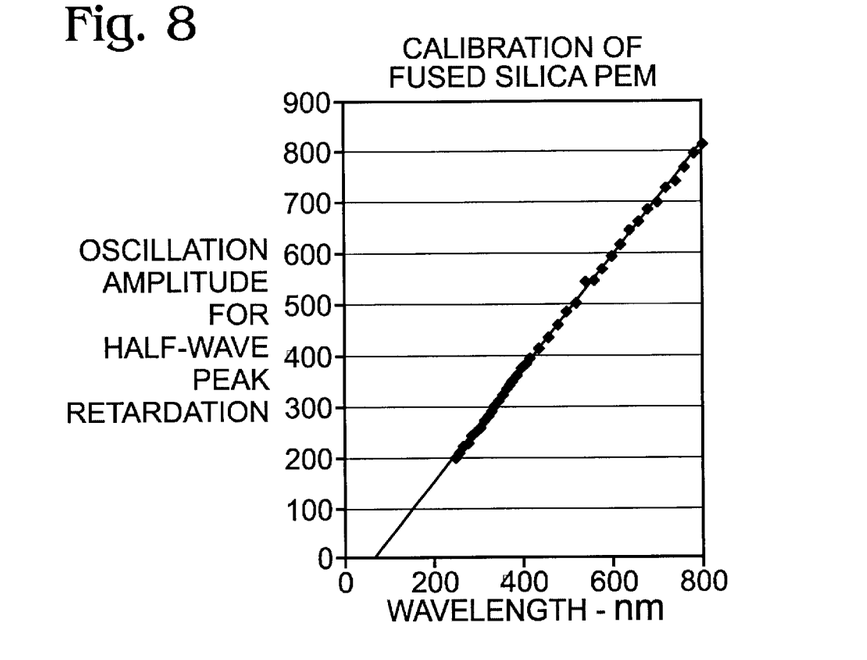
FIG. 8 is a graph that plots, for a selected retardance, the oscillation amplitude of the polarization modulator against a number of source-light wavelengths, for a polarization modulator that employs a preferred type of optical element.
Figure 9:
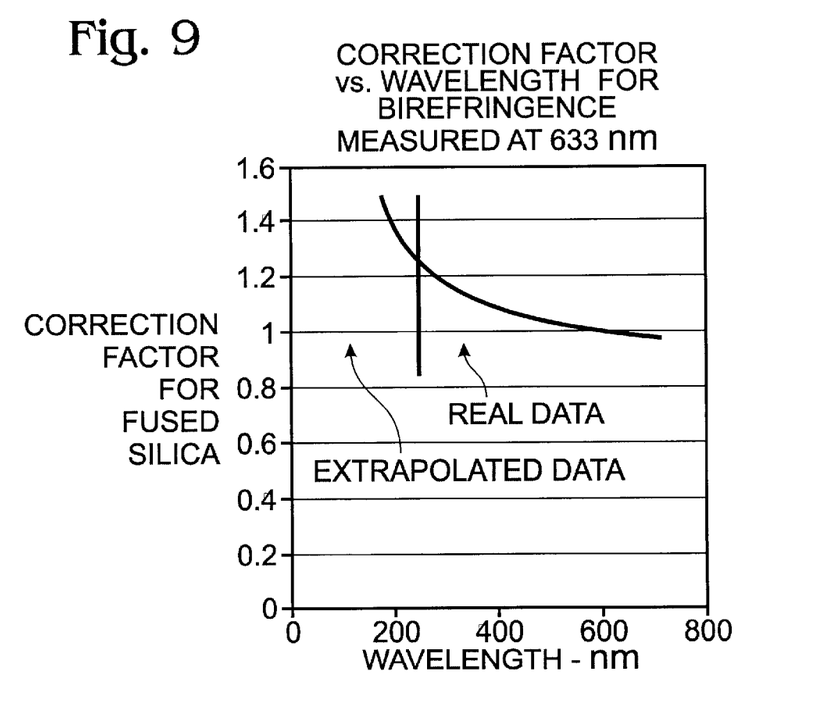
FIG. 9 is a graph, based in part on the data shown in FIG. 8, that represents a correction factor that may be applied to convert the retardance value of an optical-material sample as measured at one source-light wavelength to the retardance value that would occur in the sample at another source-light wavelength.

FIG. 9 is developed by using, in part, the plot of FIG. 8 to produce a curve that represents a correction factor that is applied to the retardance magnitude value of the sample as measured at one wavelength (such as the 632.8 nm wavelength of the HeNe laser), thereby to arrive at (either directly or by extrapolation) the retardance magnitude that would occur in the sample at other wavelengths, such as a UV wavelength of 157 nm. The data in FIG. 9 was generated from an experiment involving a PEM having a fused silica optical element for use with samples of similar fused silica material.

The wavelength correction technique just described for fused silica can also be applied to other materials. For example, FIG. 10 charts experimental results showing the oscillation amplitude required to produce, via the PEM, a selected peak retardation (such as half-wave) plotted against different source wavelengths for a PEM that employs a calcium fluoride optical element.

Figure 10:
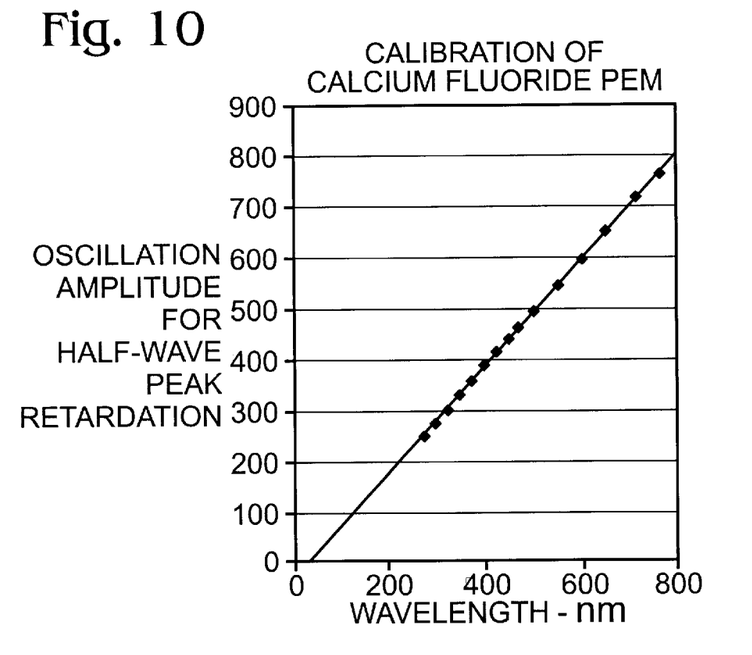
FIG. 10 is a graph that plots, for a selected retardance, the oscillation amplitude of the polarization modulator against a number of source-light wavelengths, for a polarization modulator that employs an alternative type of optical element.
Figure 11:
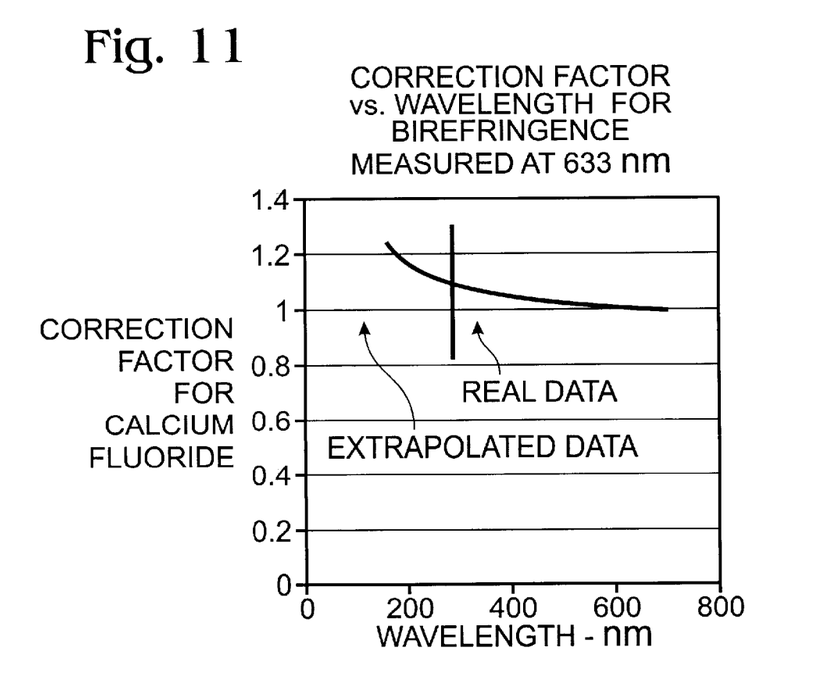
FIG. 11 is a another graph, like FIG. 9, that represents a correction factor that may be applied to convert the retardance value of an optical-material sample as measured at one source-light wavelength to the retardance value that would occur in the sample at another source-light wavelength.

FIG. 11 is developed by using the plot of FIG. 10 to produce a curve that represents a correction factor that is applied to the retardance magnitude as measured at one wavelength (such as the 633 nm wavelength of the HeNe laser), thereby to arrive at (either directly or by extrapolation) the retardance magnitude that would occur in the sample at other wavelengths, such as a UV wavelength of 157 nm. The data in FIG. 11 was generated from an experiment involving a PEM having a calcium fluoride optical element for use with samples of similar calcium fluoride material.

As another approach to correcting the measured retardation magnitude at one source-light wavelength to relate to the retardation magnitude at another wavelength, one can refer to the stress-optic coefficient of the sample material being tested, which coefficient is known as a function of wavelength. The retardance magnitudes measured at two different wavelengths are directly proportional to the stress-optic coefficient of the material.

As described above, systems according to the present invention, as exemplified in either of FIGS. 1 and 7, are calibrated to provide an accurate baseline for measuring birefringence properties of optical materials. As indicated above, variations in the baseline can be caused by changes in the environmental conditions (e.g., ambient pressure or temperature) under which the birefringence properties of a sample are measured.

For example, the optical paths and optical components of the systems of FIGS. 1 and 7 could be contained within a normally-closed chamber to prevent light emitted by laser light sources 20 from inadvertently damaging a person's vision. In addition to protecting people, such a chamber also separates the environment within the chamber from the environment of the room where the system is located. As a result of such a separation, the environment within the chamber may have steady-state environmental conditions, including ambient pressure and temperature, that differ from those in the surrounding room.

Whenever an operator opens the chamber and mounts a sample (26 or 124) on sample stage 28, the environmental conditions within the chamber typically change from their steady-state values. Despite an initial calibration to set a system baseline value, the system can be de-calibrated as the environment within the chamber returns to its steady-state conditions (e.g., "warms-up") after the chamber is closed.

Figure 12:
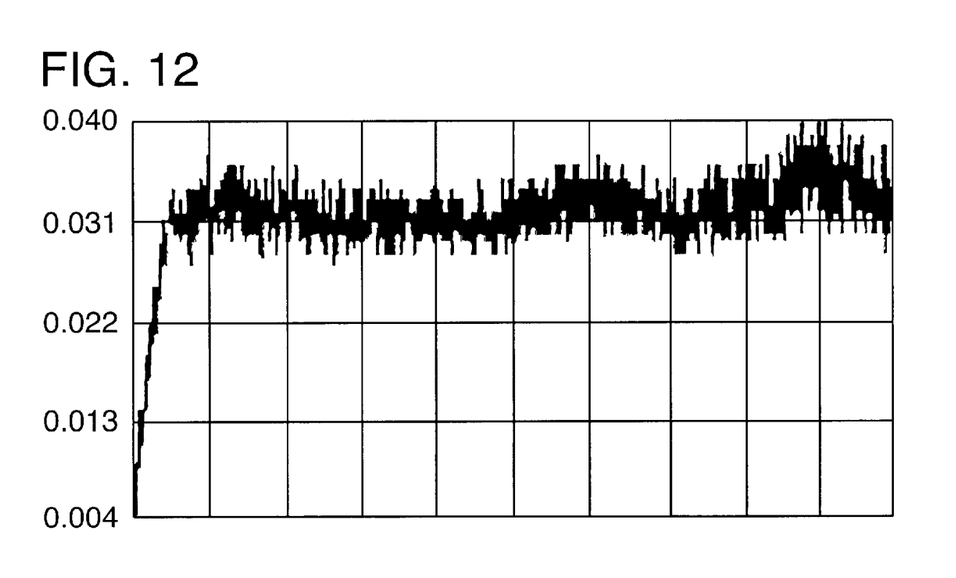
FIG. 12 is a graph that represents short-term baseline variations in a birefringence measuring system occurring at the beginning of a birefringence measurement.

FIG. 12 is a graph illustrating a measured change from the initially calibrated baseline value of a system resulting shortly after an operator opens the chamber and mounts a sample. The variations change the baseline from an initially calibrated birefringence value of 0.004 nm (i.e., nominally zero) to a value of about 0.030 nm over a period of about 4 minutes. While relatively small and brief, these variations can introduce errors into a birefringence measurement.

Figure 13:
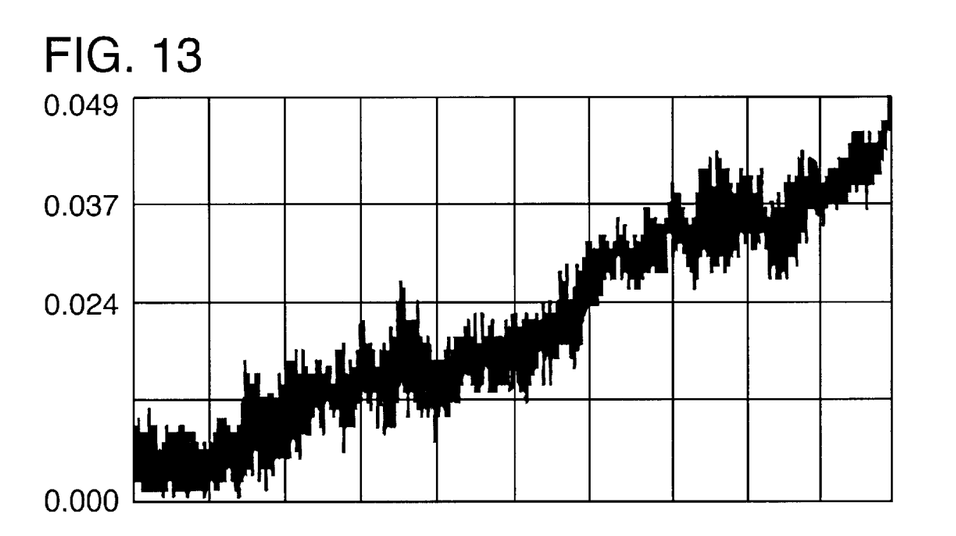
FIG. 13 is a graph that represents long-term baseline variations in a birefringence measuring system.

FIG. 13 is a graph illustrating a measured change from the initially calibrated baseline value of a system over a longer operating period resulting changes in the ambient environmental conditions in the room where the system is located. For example, the ambient pressure and temperature where the system is located can vary for a number of reasons including normally scheduled heating and cooling variations (e.g., to reduce energy costs after business hours), normal room thermostat hysteresis, heat or air flow variations caused by other adjacent machines or systems, etc. The variations change the baseline from an initially calibrated birefringence value of 0.000 nm to a value of about 0.045 nm over a period of about 4 hours. Again, while relatively small, these variations can also introduce an error into a birefringence measurement.

Figure 14:
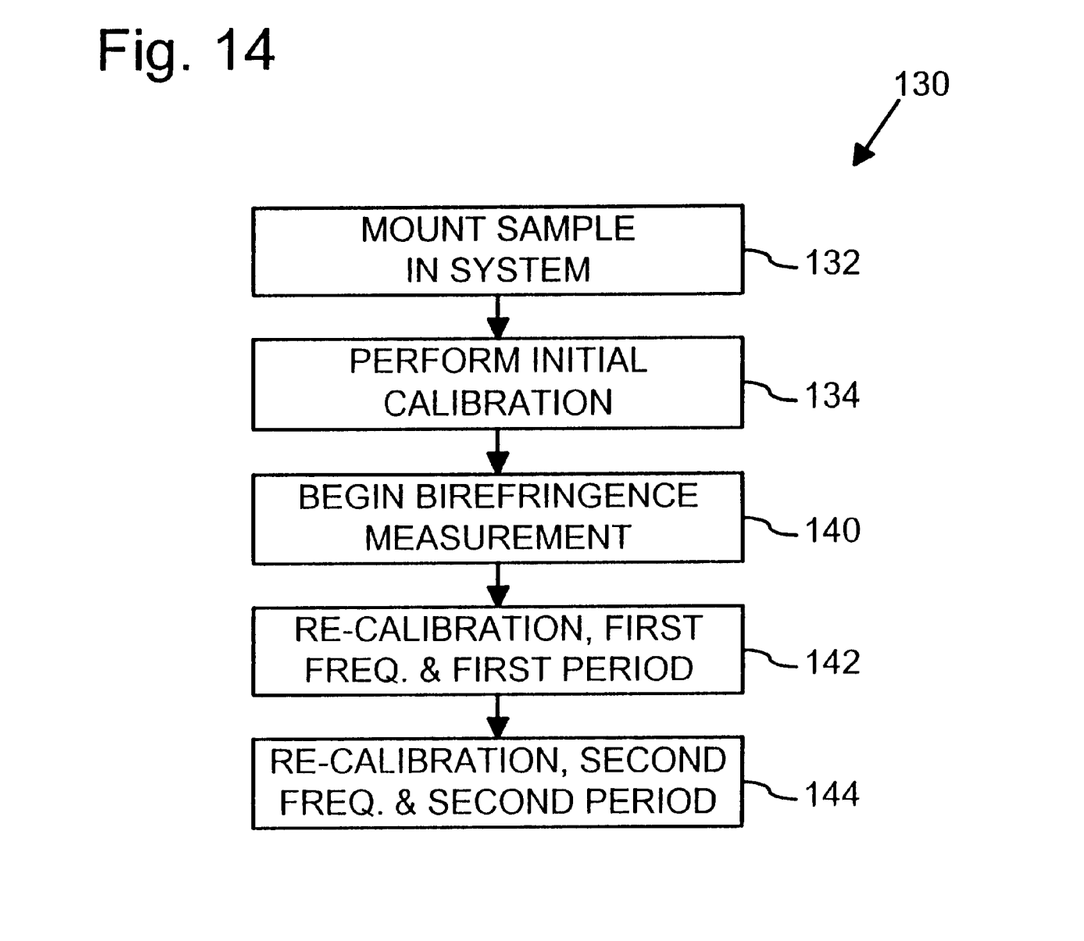
FIG. 14 is a flow diagram of a calibration method for a birefringence measurement system.

FIG. 14 is a flow diagram illustrating a dynamic self calibration process 130 by which a system according to the present invention, as exemplified in either of FIGS. 1 and 7, is periodically calibrated to provide a consistently accurate baseline for measuring birefringence properties of optical materials. In one implementation, the dynamic self calibration process periodically calibrates the system at different selected frequencies to compensate for baseline variations resulting from different causes, such as initial system warm-up or long term environmental changes in the room where the system is located.

Process block 132 indicates that a sample is mounted within a birefringence measurement system, such as one of the types shown in FIG. 1 or 7.

Process block 134 indicates that an initial calibration is performed before beginning the measurement of the birefringence properties of the sample. In a system of the type shown in FIG. 1, calibration includes aligning with light beam B an aperture 136 that extends through sample stage 28 so that light beam B passes from PEM 24 to beam splitting mirror 30 without striking sample 26. In a system of the type shown in FIG. 7, calibration includes aligning with light beam B a mirror 138 that is mounted on sample stage 28 so that light beam B passes from PEM 24 to beam splitting mirror 30 without striking sample 124. Mirror 138 includes a reflective top surface so that light beam B is reflected without passing through the transparent body of mirror 138. In both the FIG. 1 and FIG. 7 implementations, drive motors on stages 28 align aperture 136 and mirror 138 with light beams B for calibration and then re-align the sample with the light beams B to resume the measurement.

Process block 140 indicates that the measurement of the sample birefringence begins.

Process block 142 indicates that periodic re-calibration is performed at a first frequency for a first time period after the sample measurement begins. For example, the first frequency could provide re-calibration every 15–20 seconds over a first time period of about 4–5 minutes. The first time period corresponds to the nominal amount of time required for an exemplary test chamber to reach its stead-state environmental conditions after a measurement begins, as illustrated by FIG. 13. With the illustrated first frequency and first time period, the re-calibrations maintain baseline variations at the nominal noise level of the system (e.g., about 0.01 nm).

Process block 144 indicates that periodic re-calibration is performed at a second frequency for the time period following the first time period. For example, the second frequency could provide re-calibration every 10 minutes. With the illustrated second frequency, the re-calibrations maintain baseline variations at the nominal noise level of the system (e.g., about 0.01 nm).

Figure 15:
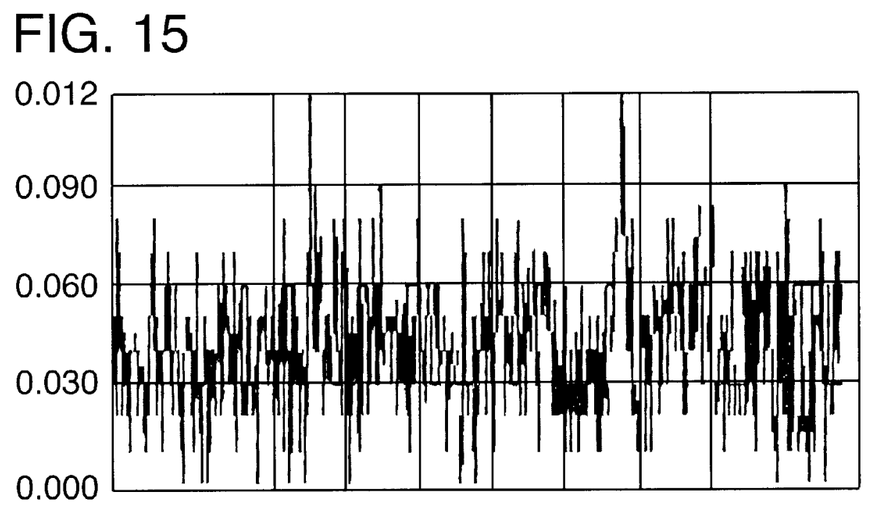
FIG. 15 is a graph illustrating a consistent baseline value, to within the nominal noise level, of a system undergoing periodic re-calibration over an initial time period according to one aspect of the present invention.
Figure 16:
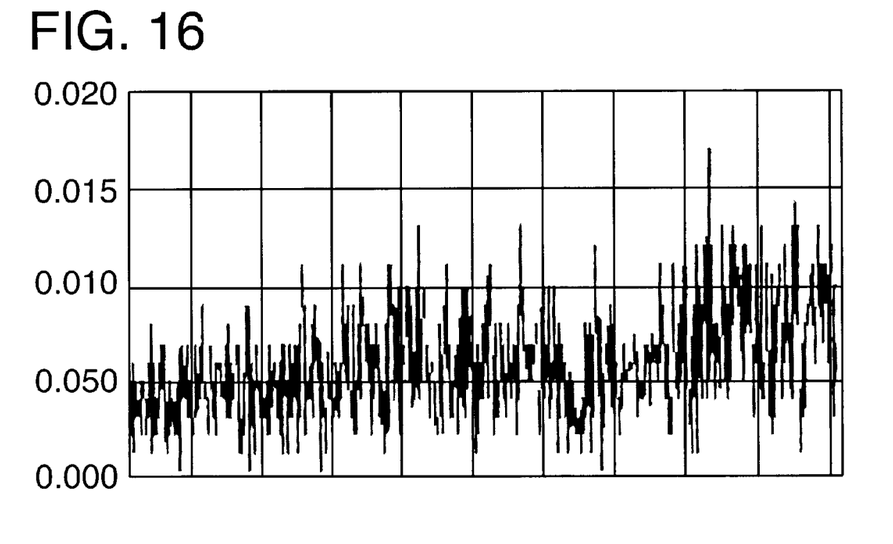
FIG. 16 is a graph illustrating a consistent baseline value, to within the nominal noise level, of a system undergoing periodic re-calibration over an extended time period according to the present invention.

FIG. 15 is a graph illustrating a consistent baseline value, to within the nominal noise level, of a system undergoing periodic re-calibration performed at a first frequency for a first time period according to process blocks 142 and 144. The illustration represents sampling over an initial period of 20 minutes, with re-calibration according to process block 142 occurring during the first 5 minutes. FIG. 16 is a graph illustrating a generally consistent baseline value, to within the nominal noise level, of a system undergoing periodic re-calibration performed over a period of about 9 hours according to process blocks 142 and 144.

Dynamic self calibration process 130 is described as periodically calibrating the system at different selected frequencies to compensate for baseline variations resulting from different causes. It will be appreciated, however, that other implementations could provide period calibration at only one of the frequencies. For example, the process could employ only periodic re-calibration during the first time period if there are no changes in the ambient environmental conditions in the room where the system is located. Similarly, if the chamber is allowed to reach its steady state conditions before beginning a measurement, the process could employ only periodic re-calibrations to compensate for variations in the ambient environmental conditions in the room where the system is located.

What is claimed is:

1. A method for calibrating a birefringence measurement system that measures birefringence properties in a sample, the method comprising:

performing an initial calibration of the system before a birefringence measurement begins;

periodically re-calibrating the system at a first frequency for a first time period after the sample measurement begins; and periodically re-calibrating the system at a second frequency after the first time period, the second frequency differing from the first frequency.

2. The method of claim 1 in which the system includes a chamber within which birefringence properties are measured and the first time period corresponds to a time for the chamber to reach steady-state environmental conditions after the birefringence measurement begins.

3. The method of claim 1 in which the system is located in an environment subject to changing environmental conditions, each calibration establishes a system baseline, and the second frequency maintains baseline variations at the nominal noise level of the system.

4. The method of claim 1 in which the second frequency provides re-calibrations less frequently than the first frequency.

5. The method of claim 1 in which the system transmits light through the sample to measure its birefringence properties and the system includes a sample stage that carries the sample and has an aperture through which light is transmitted for each calibration of the system.

6. The method of claim 1 in which the system reflects light from the sample to measure its birefringence properties and the system includes a sample stage that carries the sample and also carries a mirror from which light is reflected for each calibration of the system.

7. The method of claim 1 in which each calibration establishes a system baseline and the first frequency maintains baseline variations at the nominal noise level of the system.

8. A method for calibrating a birefringence measurement system that measures birefringence properties in a sample over a measurement period, the method comprising:

periodically calibrating the system at a first frequency for a first time period after the sample measurement begins, the first time period being less than the measurement period.

9. The method of claim 8 in which the system includes a chamber within which birefringence properties are measured and the first time period corresponds to a time for the chamber to reach steady-state environmental conditions after the birefringence measurement begins.

10. The method of claim 8 in which each calibration establishes a system baseline and the first frequency maintains baseline variations at less than 10% of the overall baseline variation that would otherwise occur over the first time period.

11. The method of claim 8 further comprising periodically re-calibrating the system at a second frequency after the first time period, the second frequency differing from the first frequency.

12. The method of claim 11 in which the second frequency provides re-calibrations less frequently than the first frequency.

13. The method of claim 11 in which the system is located in an environment subject to changing environmental conditions, each calibration establishes a system baseline, and the second frequency maintains baseline variations at the nominal noise level of the system.

14. A method for calibrating a birefringence measurement system that measures birefringence properties in a sample that is mounted within a measurement chamber, the method comprising:

mounting the sample within the measurement chamber, the chamber having environmental conditions therein;

performing an initial calibration of the system before a birefringence measurement begins; and after the environmental conditions within the chamber reach steady-state conditions, periodically re-calibrating the system at a selected frequency for the duration of the measurement.

15. The method of claim 14 in which the system is located in an environment subject to changing environmental conditions, each calibration establishes a system baseline, and the selected frequency maintains baseline variations at the nominal noise level of the system.

* * * * *